United States Patent [19]

Borsaru et al.

[11] 4,361,534

[45] Nov. 30, 1982

[54] NEUTRON ACTIVATION ANALYSIS

[75] Inventors: Mihai Borsaru; Peter L. Eisler, both of Victoria, Australia

[73] Assignee: Commonwealth Scientific and Industrial Research Organization, Campbell, Australia

[21] Appl. No.: 175,799

[22] Filed: Aug. 6, 1980

[30] Foreign Application Priority Data

Aug. 6, 1979 [AU] Australia ............................. PD9897

[51] Int. Cl.³ .............................................. G21G 1/06
[52] U.S. Cl. ..................................... 376/159; 376/163
[58] Field of Search .................. 176/10; 250/302, 303, 250/270, 253, 255, 356, 358 R; 376/159, 163

[56] References Cited

U.S. PATENT DOCUMENTS

| | | | |
|---|---|---|---|
| 3,008,047 | 11/1961 | Earley et al. | 250/255 |
| 3,035,174 | 5/1962 | Turner et al. | 250/270 |
| 3,463,922 | 8/1969 | Senftle et al. | 250/253 |
| 3,665,195 | 5/1972 | Youmans | 250/270 |
| 3,781,545 | 12/1973 | Paap et al. | 250/270 |
| 3,781,556 | 12/1973 | Taylor et al. | 250/303 |
| 3,889,112 | 6/1975 | Holmes et al. | 250/255 |
| 4,090,074 | 5/1978 | Watt et al. | 250/358 R |

FOREIGN PATENT DOCUMENTS 478970 3/1973 Australia .

OTHER PUBLICATIONS

Ann. Inst. Geol. Publici Hungary, vol. 54, pp. 375-386, (1970), Dugain et al.
Anal. Chim. Acta, vol. 70, pp. 253-263, (1974), vol. 78, pp. 329-341, (1975), Alaerts et al.
Pure Appl. Chem., vol. 49, pp. 1555-1573, (1977) Gijbels et al.
Nucl. Appl. Technol., vol. 8, pp. 465-473 (1970), Kuusi.
Analytical Chemistry, vol. 48, No. 12, 10/76, pp. 1699-1701, Borsaru et al.
J. of Radioanalytical Chemistry, vol. 31, No. 1, 1976, pp. 325-333, Janczyszn et al.

Primary Examiner—Harvey E. Behrend
Attorney, Agent, or Firm—Sughrue, Mion, Zinn, Macpeak & Seas

[57] ABSTRACT

Neutron activation is used to analyse the silicon and aluminium content of samples of material, such as bauxite ore and coal. The analysis can be performed on bulk samples, on material on a moving conveyor belt, or on the walls of a borehole. The method involves high energy neutron irradiation of the sample, measurement of the thermal neutron flux in the sample, and monitoring the gamma radiation from the sample at energies of (a) 1.78 MeV and (b) 0.844 MeV and/or 1.015 MeV. Such gamma radiation is produced on decay of (a) $^{28}$Al and (b) $^{27}$Mg isotopes, produced by the reactions $^{28}$Si(n,p)$^{28}$Al and $^{27}$Al(n,p)$^{27}$Mg. A single gamma ray detector is used. The analysis preferably utilizes equations which include terms to compensate for (a) the production of radiation at 1.78 MeV as a result of the production of the isotope $^{28}$Al from $^{27}$Al by the thermal neutron reaction $^{27}$Al(n,$\gamma$)$^{28}$Al, and (b) the Compton scattering of 1.78 MeV gamma radiation and background.

20 Claims, 4 Drawing Figures

NEUTRON ACTIVATION ANALYSIS

This invention concerns the simultaneous measurement of the chemical concentrations of the silicon and aluminium constituents of materials. It provides both a method and apparatus for that purpose. There are many possible applications of the present invention, including the measurement of silicon and aluminium in coal and in iron ores. However, the invention was developed primarily to permit the monitoring of the chemical concentrations of aluminium and silicon in bauxite ores, as part of a quality control process for the mineral industry, and it is this application of the invention that will be described in detail in this specification.

There are two particular areas in the bauxite industry where the present invention will be used. One is the monitoring of ore quality during ship-loading operations of bauxite for export, where monitoring of aluminium grade and silicon impurity concentrations are essential to ensure that the ore satisfies export contract specifications. The other use is the monitoring of ore quality whilst sorting the bauxite into stockpiles of different specified chemical concentrations of silicon and aluminium. Depending on the way in which they have been formed, these stockpiles (a) may contain ore which has been blended for ore treatment plants or (b) may be used in subsequent blending operations.

In both of these situations, the current practice in monitoring the ore quality involves the periodic sampling of the ore from the bulk supply, which is usually moving on a conveyor belt when the sample is taken. The samples are moderately large (several kilogrammes) and are either subsampled immediately, or are mixed with other samples, taken by a predetermined number of automatic sampling cycles to form a representative bulk sample, which is then sub-sampled. Sub-sampling and crushing proceeds until a small specimen (of about 1 g) is ultimately available for chemical analysis by wet chemical assaying or by X-ray fluorescence analysis procedures. These sample preparation procedures are particularly time-consuming if good representivity of the bulk is required in the sample. The analysis is also time-consuming.

It has been found that in some situations (for instance during ship loading), when variations of ore quality occur these analytical methods are not fast enough to permit steps to be taken to correct the chemical concentrations of aluminium and silicon (for example, by further blending measures). If it were possible to apply the prior art techniques to on-stream analysis of bauxite on a moving belt, a more rapid analysis of the constituents and hence more rapid corrective blending measures should, in principle, be possible. Unfortunately, wet chemical methods cannot be applied to an on-stream situation, and on-stream X-ray fluorescence methods are inapplicable to lump-flow measurement. The X-ray fluorescence method is also unsuitable for the analysis of untreated bulk samples, due to the low penetration of X-radiation (less than 1 mm), and the fact that the ore is heterogeneous as regards moisture and particle size.

Neutron activation analysis, which is the basis of the present invention, does not have the problems associated with wet chemical assaying or the X-ray fluorescence technique, noted above, when applied to the analysis of large bulk samples. Indeed, activation analysis methods are directly applicable to large bulk samples and require minimal sample preparation in terms of crushing and drying. They also avoid most of the heterogeneity problems associated with the application of X-ray fluorescence analysis to bulk samples because the neutrons and gamma rays involved have a much deeper penetration than X-rays. For this reason, the monitoring of bauxite ore quality (and the aluminium and silicon content of other materials) on moving belts is amenable to the neutron activation method of the present invention.

Neutron activation methods have previously been applied to the analysis of silicon and aluminium in small samples (less than 150 g). For example, they have been described in the paper by F. Dugain and J. Tatar in *Ann. Inst. Geol. Publici* Hungary, Volume 54, p 375 (1970), and in the papers by L. Alaerts, J. P. Op de Beeck, and J. Hoste, in *Anal. Chim. Acta*, Volume 70, p 253 (1974) and in *Anal. Chim. Acta*, Volume 78, p 329 (1975). These methods depend on two interactions with the constituent chemical elements. One interaction is that occurring between fast neutrons and $^{28}$Si, producing $^{28}$Al by the reaction $^{28}$Si(n,p)$^{28}$Al. The product, $^{28}$Al, decays with a 2.3 minute half life, emitting 1.78 MeV gamma radiation. Similarly, when the aluminium constituent of the sample is irradiated with slow neutrons, the same radioactive isotope, $^{28}$Al, is produced with the consequent emission of 1.78 MeV gamma radiation. Since there is negligible interaction between the fast neutrons and the material in small samples, the chemical concentrations of silicon and aluminium can be calibrated directly against the number of 1.78 MeV gamma ray counts observed within a given time interval after irradiation first with fast neutrons and then with slow neutrons. With bulk samples of bauxite, particularly samples having a significant water content, special allowance must be made for the slowing down of the fast neutrons used for the silicon analysis and the associated production of $^{28}$Al due to the capture of slow neutrons by the aluminium during the same irradiation. One method of allowing for this effect is described below, in the description of the operation of the present invention.

For the currently used neutron activation analysis techniques, because two irradiations are necessary (with fast, then slow neutrons), there is a considerable capital outlay on the two neutron sources and their respective shielding assemblies. If the analysis is applied to a moving stream of ore on a belt, two spectrometric gamma ray detectors [for example, 127×127 mm NaI(Tl)] are also required. If the analysis is performed on bulk samples contained in bins or boxes, although only one gamma ray detector is necessary, the analysis procedures for silicon and aluminium must duplicate each other, which doubles the necessary time and effort for analysis. In addition, for the measurements to be useful to the analyst, it is essential that the fast and slow neutron flux should be constant and reproducible from one measurement to the next.

The present invention offers appreciable savings in time and equipment cost, compared with current technology, by providing a method of analysis which is based on a single sample irradiation followed by a single measurement procedure.

The nuclear reactions providing the basis of the present invention are:

$^{27}$Al(n,p)$^{27}$Mg (used for the determination of the aluminium constituent), and $^{28}$Si(n,p)$^{28}$Al (for the silicon determination).

The energies of neutrons effective in these reactions are greater than 4.5 MeV. The radioactive nucleus $^{27}$Mg decays with a half life of 9.46 minutes and emits two gamma rays during its decay, which have energies of 0.844 MeV and 1.055 MeV respectively. The emission and half life of the other radioactive nucleus, $^{28}$Al, have been described above. As previously mentioned, a third nuclear reaction is important with all bulk samples having significant water content as well as aluminium and silicon constituents. This reaction, $^{27}$Al(n,$\gamma$)$^{28}$Al, which entails the capture of slow neutrons in aluminium, results in the emission of 1.78 MeV gamma radiation which is additional to the 1.78 MeV gamma radiation resulting from the fast neutron reaction with the silicon constituent of the sample. (Note that even with sources emitting only fast neutrons for sample irradiations, appreciable numbers of fast neutrons are slowed down to thermal energies within the sample by their collision with the hydrogen nuclei associated with the water content of the sample).

Applications of the above nuclear reactions for the fast neutron activation analysis of aluminium and silicon have been described in the scientific literature. For example, reference can be made to the paper by R. H. Gijbels and J. Hertogen in *Pure Appl. Chem.*, Volume 49, p 1555, (1977), and the paper by J. Kuusi in *Nucl. Appl. Technol.*, Volume 8, p 465 (1970). However, these applications are either for small samples, or for larger samples that contain little hydrogen and therefore cause negligible moderation of the fast neutrons within the samples.

The present invention overcomes the problem of interference by aluminium with silicon from the 1.78 MeV gamma radiation in the following way. After the fast neutron irradiation, the 1.78 MeV gamma rays from the sample are measured concurrently with those emitted by $^{27}$Mg at 0.844 MeV and 1.015 MeV for a preset time interval. (If the sample container is fabricated from a material such as copper, which produces gamma radiation interfering with the 1.015 MeV gamma rays of the sample, the 1.015 MeV gamma rays are excluded from the analysis). Since the number of counts from $^{27}$Mg are due only to aluminium, the chemical concentration of aluminium can be related directly to these recorded counts, given a knowledge of the mass of the sample. With a knowledge of the aluminium content of the sample, provided the slow neutron flux in the material is also known, the component of the 1.78 MeV gamma radiation due to slow neutron reactions with the aluminium can be subtracted from the total 1.78 MeV gamma radiation count to provide the gamma radiation at 1.78 MeV resulting from fast neutron activation of the silicon in the sample.

Because the thermal neutron flux within the bulk sample is sensitive to water content, it is essential to measure the number of thermal neutrons in a given time interval during the neutron irradiation. For this purpose, a suitable neutron detector will be located adjacent to the sample. The number of neutrons recorded by the detector is proportional to the thermal neutron flux within the sample.

Thus, according to the present invention, a method of simultaneously analysing the aluminium and silicon content of a sample of material comprises the steps of:

(a) irradiating the sample with fast neutrons;

(b) monitoring the thermal neutron flux within the sample;

(c) monitoring the gamma radiation from the irradiated sample at energies of 1.78 MeV and 1.015 and/or 0.844 MeV;

(d) using the monitored gamma radiation at 1.015 and/or 0.844 MeV to estimate the aluminium content of the sample; and (e) using the monitored gamma radiation at 1.78 MeV, compensated by the gamma radiation at 1.78 MeV due to the thermal neutron reaction with the estimated aluminium in the sample, to estimate the silicon content of the sample.

Also according to the present invention, apparatus for the simultaneous analysis of aluminium and silicon content of a sample of material comprises:

(a) a fast neutron source, adapted to irradiate the sample of material;

(b) a thermal neutron detector, located to monitor the thermal neutron flux in the irradiated sample; and (c) a gamma ray detector separated from the neutron source and shielded therefrom, adapted to monitor the gamma spectrum from the irradiated sample, at least at energies of 1.78 MeV and of 0.844 and/or 1.015 MeV.

Other features of the present invention will become apparent from the following description of an embodiment of the invention, in which reference will be made to the accompanying drawings, of which:

Figure 1:
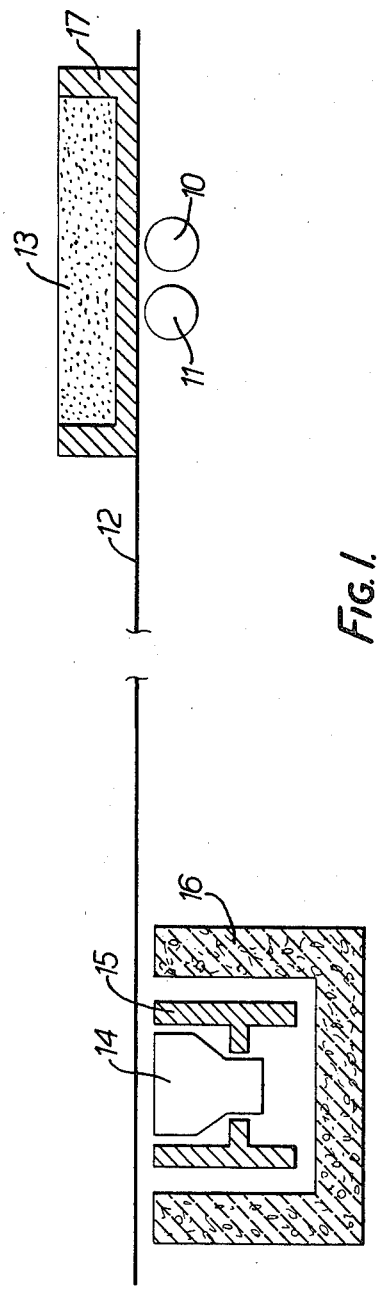
FIG. 1 is a schematic diagram of an experimental arrangement for the measurement of the aluminium and silicon content of a sample.

Before describing the apparatus and technique in detail it will be helpful to consider the mathematics associated with the present invention.

In a sample containing both aluminium and silicon, the grade of aluminium, Al, is related to the number of counts, G, recorded of gamma rays emitted by $^{27}$Mg at 0.844 MeV and/or 1.015 MeV, and to the sample weight, W, by the equation:

$$Al = a_0 + a_1 G + a_2 W. \qquad (1)$$

The constant coefficients $a_0$, $a_1$ and $a_2$ are determined from linear regression analysis by calibrating the responses G and W of the apparatus against the aluminium content of known samples using linear regression analysis.

The number of counts G is determined from the equation $$G = G_T - kJ, \qquad (2)$$

where $G_T$ is the total number of gamma rays recorded in an energy window encompassing the 0.844 MeV and/or 1.015 peaks, J is the total number of counts recorded of 1.78 MeV gamma rays, and k is a constant. The term kJ is used to subtract the spectral continuum due to both the Compton scattered 1.78 MeV gamma radiation and background due to the neutron source.

Thus $$Al = a_0 + a_1 G_T + a_2 W + a_3 J, \qquad (3)$$

where $a_3 = -a_1 K$.

Similarly, the chemical concentration of silicon, Si, in the sample can be related to the number of counts per unit time, H, of 1.78 MeV gamma rays due to the $^{28}Si(n,p)^{28}Al$ reaction and the sample weight, W, by:

$$Si = b_0 + b_1 H + b_2 W, \quad (4)$$

where $b_0$, $b_1$ and $b_2$ are constant coefficients obtainable from regression analysis by calibrating the responses H and W against the silicon content of known samples using linear regression analysis.

In practice, with bulk bauxite samples, however, the total number of counts per unit time due to 1.78 MeV gamma rays from $^{28}Al$, J, contains two indistinguishable components H and I, where I is the component contributed by thermal neutron activation of $^{27}Al$. The number of counts, I, is proportional to the product of the number of thermal neutrons, $N_t$, measured during irradiation and the aluminium concentration of the sample. Because the number of counts, $G_T$, previously referred to, are related to the aluminium concentration, and since $N_t$ is proportional to the thermal neutron flux within the sample, the actual silicon concentration in the sample is given by:

$$Si = b_0 + b_3 J + b_4 G_T N_t + b_2 W, \quad (5)$$

where $b_3$ and $b_4$ are regression coefficients, and where $b_0$, $b_2$, $b_3$ and $b_4$ are calibration coefficients determined by linear regression analysis as described above.

Equations (3) and (5) are used in analysis of materials in accordance with the present invention.

The experimental arrangement devised to test the present invention, and illustrated in FIG. 1, comprises a neutron source 10 and thermal neutron detector 11 located close to a railway track 12 on which a small sample of material 13 can be moved. Also close to the track 12, but remote from the neutron source 10 and detector 11, is a gamma ray detector 14, suitably shielded by a lead screen 15 and a masonry shield 16.

In the experimental facility shown in FIG. 1, the neutron source was 20 Ci of Am-Be, giving an estimated output of $4.4 \times 10^7$ n/s. The samples of material 13 were contained in a rectangular brass box 17 ($25 \times 25 \times 4$ cm deep) and were irradiated by fast neutrons from underneath. The neutron source 10 was enclosed within a cyclindrical shell 21 of cadmium (see FIG. 2) which prevented the thermal neutrons emitted by the source from reaching the sample 13. The thermal neutron flux generated within the sample 13 was monitored by thermal neutron detector 11, which was a high efficiency neutron detector (filled to a pressure of 4 atmospheres with a mixture of $^3He$ and Kr) which was also located beneath the sample container and adjacent to the neutron source.

After irradiation by source 10 for 6 minutes, the sample 13 was transferred within 15 seconds to a position immediately above the gamma detector 14, which comprised a $127 \times 127$ mm NaI(Tl) scintillation detector. The distance between the neutron source 10 and gamma detector 14 was about 7 meters. This separation between source and detector added a considerable component of distance shielding to the already appreciable shielding against source radiation provided by concrete brick structures 16 and 26 built around both the NaI(Tl) detector 14 and the neutron source assemblies. The lead shield 15, of thickness 3 cm, which was built around the body of the scintillation detector 14 so as to leave only the upper plane surface exposed for measurements, provided further reduction of background radiation.

Spectrum stabilization was obtained using 0.662 MeV gamma rays from a $^{137}Cs$ source (not shown in the drawings) which provided a reference peak for a Canberra Industries Model 1520 analogue spectrum stabilizer.

Figure 2:
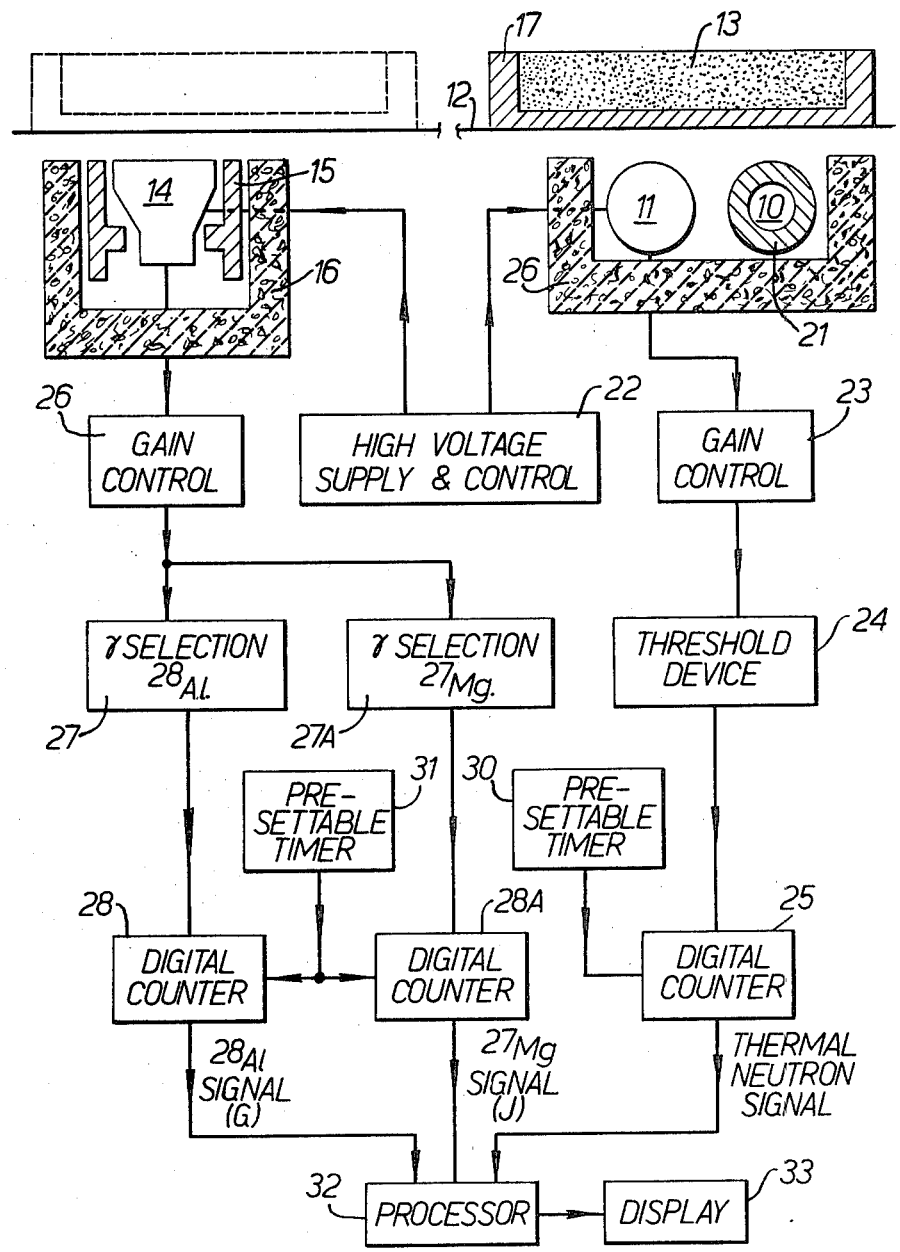
FIG. 2 is a diagram, partly schematic and partly in block form, illustrating the components used in the neutron activation analysis arrangement illustrated in FIG. 1.

The energy spectra of gamma rays detected by the scintillation detector 14 were analysed in the initial phases of the development of the method by a Tracor Northern 4096-channel pulse height analyser (model TN-1700). At a later stage, when energy-pulse height calibrations had been fully established, Ortec single channel analysers, digital counters and a timer were used, as shown in FIG. 2, for their greater suitability to plant or mine site operating requirements. The amplifiers used were a Tennelec linear amplifier for the scintillation detector 14 and an Ortec spectroscopy amplifier for the neutron detector 11. Output from the digital counters was obtained with a strip printer.

The partly schematic and partly block form diagram of FIG. 2 is essentially a more comprehensive illustration of the apparatus shown in FIG. 1. In particular, the high energy neutron source 10 and the thermal neutron detector 11 are shown more explicitly, with the neutron source 10 encased in cadmium shielding 21 and the source 10 and detector 11 positioned within masonry shielding 26.

A single high voltage power supply 22 services both the thermal neutron detector 11 and the gamma ray detector 14.

The output signal from the thermal neutron detector 11 is first amplified in gain control unit 23, and if the signal, when amplified, exceeds a required threshold value (determined by threshold device 24), it is supplied to the input of a digital counter 25. The output from counter 25 is fed into processor 32, which is usually a microprocessor or small computer, programmed to effect the required analysis from its three input signals.

The other two input signals to the processor 32 are signals indicative of the values G and J (see the above description). These signals are derived from the gamma rays received by the gamma detector 14 as a result of the decay of, respectively, the $^{28}Al$ and $^{27}Mg$ isotopes formed during the irradiation of the sample. These inputs are obtained after the output of detector 14 has been processed by amplifier 26, a gamma ray discriminator, and digital counters 28 and 28A. The gamma ray discriminator has been shown in the drawing as two gamma ray single channel analysers 27 and 27A. In practice, these devices 27 and 27A may be a single unit comprising a multi-channel analyser with outputs from channels which have energy windows, typically about 0.35 MeV wide, centred on 0.844 MeV, 1.015 MeV and 1.78 MeV.

Presettable timer 31 controls the operation of the digital counters 28 and 28A. Timer 31 will be synchronized with, but operating sequentially to, pre-settable timer 30 which controls the operation of the digital counter 25.

The output from the processor 32 may be recorded. For example, it may be stored on magnetic tape, magnetic disc, magnetic card, punched tape, punched card, or on any other suitable medium. Alternatively, or additionally, the output from the processor 32 may be presented as a digital display, a paper print-out, or on a chart recorder. Those skilled in this field will appreciate that the actual form of the presentation of the output from processor 32 may be chosen to suit the requirements of the owner or operator of the equipment. Accordingly, a single, unspecified display unit 33 has been included in FIG. 2.

In one example of the experimental testing of the present invention, bauxite samples were dried to less than 5 percent (by weight) free moisture and crushed to −6 mm particle size. It should be noted, however, that this amount of pre-treatment is not essential. The bauxite samples contained aluminium in the range from 26 wt. percent to 32 wt. percent, whilst the silicon concentrations ranged from 0.9 wt. percent to 4.5 wt. percent. The mass of the sample used for irradiation was about 4 kg.

As expected, when the bauxite was irradiated with fast neutrons, the gamma ray spectra were dominated by the 1.78 MeV gamma ray peak due to $^{28}$Al, and by a spectral continuum of gamma rays which had undergone Compton scattering both within the detector and within the bulk sample. This continuum underlies the spectral peaks at 1.015 and 0.844 MeV due to $^{27}$Mg. The Comptom scattering processes in this example were dominated by gamma rays which initially had energies of 1.78 MeV, 1.014 MeV and 0.844 MeV originating from the sample, and 0.662 MeV due to the $^{137}$Cs stabilization reference source. In the case of bauxite, again as expected, the interferences from other constituents, such as the natural radioactive nuclides, was minimal, and those from $^{56}$Mn at 0.846 MeV, 1.811 MeV and 2.113 MeV were very small. (This nuclide, with a 2.57 hr. half life, can arise from the $^{55}$Mn(n,$\gamma$)$^{56}$Mn reaction, or from a $^{56}$Fe(n,p)$^{56}$Mn reaction; the first of these reactions will contribute negligible $^{56}$Mn owing to the extremely low concentration of manganese in Australian bauxites, despite the relatively large cross section of 13.3 barns for that reaction; the second reaction, involving iron, contributes more $^{56}$Mn than the first, but constitutes a constant level of about 2 percent interference, the variation of which is only about 1 percent of the gamma ray signal from $^{27}$Mg.)

Another source of spectral interference which occurred in this example arose from the neutron activation of the copper constituent of the brass sample container, which contributed a small peak at 1.05 MeV. It was necessary, therefore, to exclude from calculations all count data that would have been recorded in a narrow energy window, about 0.1 MeV wide, centred at 1.05 MeV.

Apart from interferences to the spectral peaks due to $^{28}$Al and $^{27}$Mg from monoenergetic gamma rays emitted by minor constituents of the sample and sample container, there was also substantial interference from the continuum of scattered gamma radiation. The extent of interference with the 1.78 MeV spectral peak appeared to be insignificant owing to negligible gamma radiation apparent at higher energies. However, the 0.844 MeV gamma ray peak due to $^{27}$Mg received considerable interference from the substantial underlying continuum caused by Compton scattering of the 1.78 MeV gamma radiation from the decay of $^{28}$Al and background from the neutron source.

One technique that could have been used to overcome the interference problem when using multichannel pulse height analysers for neutron activation analysis is that which is described in the specification of Australian Pat. No. 468,970. That method entails an estimation of the underlying continuum which is based on the number of counts in an energy channel close to the relevant spectral peak. However, in the present experimental arrangement, an alternative method was effectively implemented with the use of single channel analysers for the activation analysis of bauxite. The method simply entailed the establishment of two particular energy windows. One window, centred at 0.844 MeV, is approximately 0.1 MeV wide. The other window, about 0.35 MeV wide, encompasses the 1.78 MeV peak.

Implementation of these two energy-window conditions alone worked well because the counts accumulated within the spectral continuum occurring within the first narrow window are proportional, with good approximation, to the number of counts due to $^{28}$Al, 1.78 MeV gamma radiation. The counts recorded in these two windows were respectively denoted by $G_T$ and J in equations (3) and (5) for purposes of either determining the calibration coefficients, $a_i$ and $b_j$, or for determining the chemical concentrations of silicon and aluminium in samples when calibrations, and hence coefficients, were already known.

After performing a number of experiments with well-blended, effectively homogeneous, ore samples of accurately known composition, the data from the activation analysis were fitted against the known chemical assays for aluminium and silicon by linear regression analysis, in order to determine the constant coefficients in equations (3) and (5). The respective precisions for silicon and aluminium determinations in bulk samples were obtained in terms of the sample standard deviations (s) as shown below:

(a) When using equations (3) and (5), and the method of the present invention,
  for Al: s=0.43 percent Al
  for Si: s=0.14 percent Si
(b) When the contribution by gamma rays from $^{27}$Mg at 0.844 MeV is omitted from equation 5,
  for Si: s=0.19 percent Si
(c) When the contributions both by the gamma rays from $^{27}$Mg at 0.844 MeV and thermal neutrons measured below the sample container are omitted from equation 5,
  for Si: s=0.82 percent Si As shown by the smaller standard deviations for the results obtained using the present invention, the present invention compares most favourably with alternatives (b) and (c).

Figure 3:
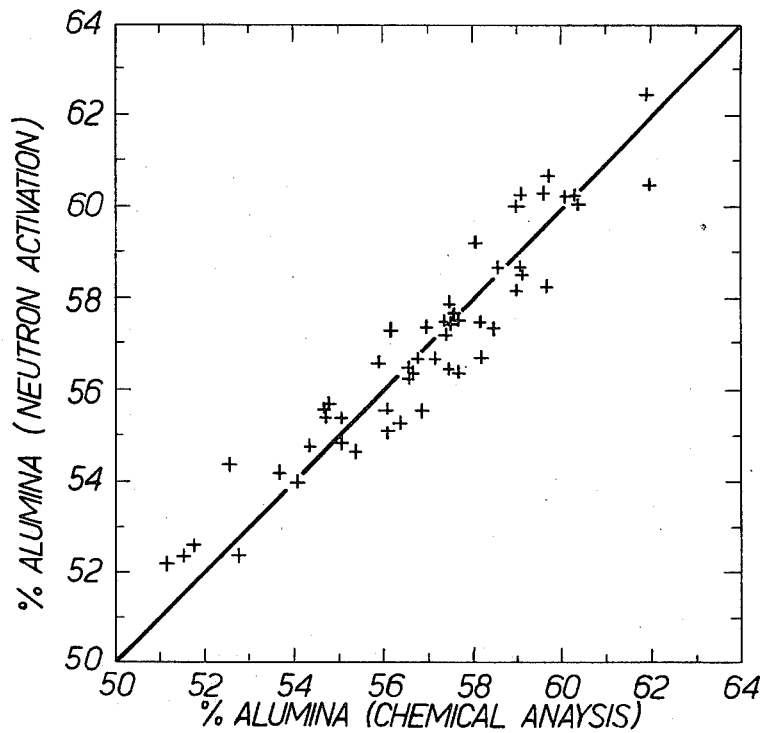
FIGS. 3 and 4 are graphs displaying the results of aluminium and silicon determinations in samples which have been subjected to both conventional analysis and analysis by the neutron activation technique of the present invention.
Figure 4:
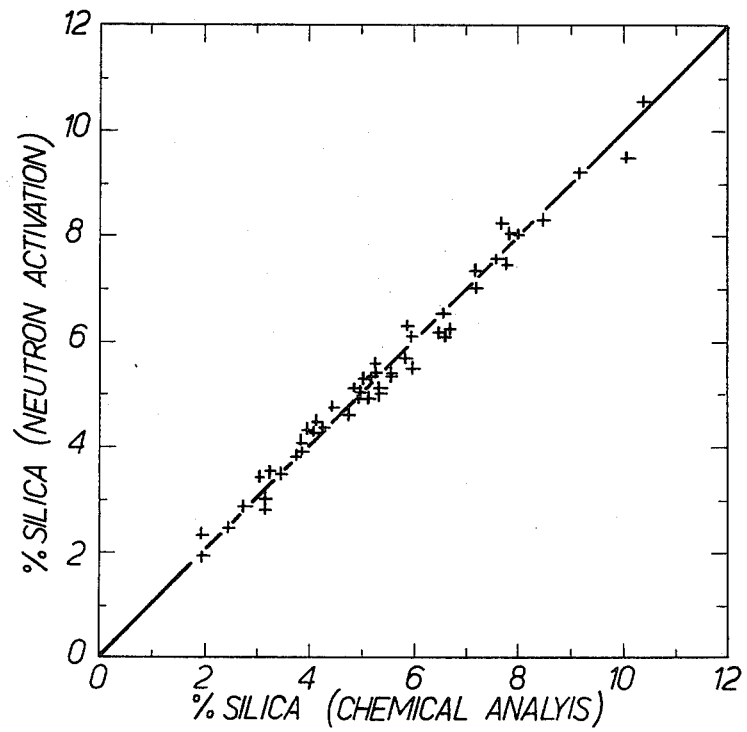

Comparisons between neutron activation determinations for aluminium and silicon, expressed as alumina ($Al_2O_3$) and silica ($SiO_2$) respectively, and determinations by conventional analysis are shown in FIGS. 3 and 4. The calibration equations used to calculate the neutron activation determinations of alumina and silica in FIGS. 3 and 4 were as follows:

$$Al_2O_3 = 71.04 - 0.946 G_T - 9.636 W - 0.242 J \quad (6)$$

$$SiO_2 = 12.93 + 0.665 J - 0.0477 G_T N_t - 2.61 W \quad (7)$$

where J and $G_T$ are expressed in thousands of counts, $N_t$ in millions of counts, and W in kilograms.

It will be clear to those skilled in this art that (a) the container 17 need not be of brass and thus need not generate a significant component of the gamma spectra being studied, (b) the rail and bulk sample of the experimental arrangement described above can be substituted by a conveyor belt carrying ore (or other material) between a neutron irradiation station and a downstream gamma monitoring station, to enable on-stream analysis for silicon and aluminium of the material being carried by the belt, and (c) the rail and bulk sample of the experimental arrangement described above can be substituted by the stationary walls and surrounding rock of a borehole, and both the source and detector can be simultaneously moved in the borehole to enable borehole logging for silicon and aluminium. For such an arrangement, the high energy neutron source, the thermal neutron detector and the gamma ray detector will be mounted on a borehole probe, which can then be lowered into a borehole to any required position to analyse the rock surrounding the borehole. Normally the signal processing equipment will not be included on the probe, but will be connected to the source and detectors by long cables.

We claim:

1. A method of simultaneously analysing the aluminium and silicon content of a sample of material using only a single irradiation from a single neutron source, comprises the steps of:
   (a) irradiating the sample only with fast neutrons from said single neutron source,
   (b) monitoring the thermal neutron flux within the sample, which flux results from moderation of the fast neutrons within the sample material,
   (c) monitoring the gamma radiation from the irradiated sample at 1.78 MeV and at an energy selected from the group consisting of (1) 1.015 MeV, (2) 0.844 MeV and (3) 1.015 and 0.844 MeV;
   (d) using the monitored gamma radiation of energy selected from said group to estimate the aluminium content of the sample; and
   (e) using the monitored gamma radiation at 1.78 MeV, compensated by the gamma radiation at 1.78 MeV due to the thermal neutron reaction with the estimated aluminium in the sample, to estimate the silicon content of the sample.

2. A method as defined in claim 1, in which step (c) includes compensating the measured gamma radiation at an energy selected from said group for Compton scattered 1.78 MeV gamma radiation and background gamma radiation.

3. A method as defined in claim 1 or claim 2, in which the determination of the aluminum content of the sample in step (d) is effected using the equation $$Al = a_0 + a_1 G_T + a_2 W + a_3 J$$

where $a_0$, $a_1$, $a_2$ and $a_3$ are calibration coefficients that are determined by calibrating the responses $G_T$, W and J against the aluminum content of known samples using regression analysis, $G_T$ is the total number of gamma detector counts in unit time of gamma rays having an energy selected from said group, J is the total number of gamma detector counts in unit time having an energy of 1.78 MeV, and W is the weight of the sample.

4. A method as defined in claim 3, in which the determination of the silicon content in step (e) is effected using the equation $$Si = b_0 + b_3 J + b_4 G_T N_t + b_2 W,$$

where $b_0$, $b_2$, $b_3$ and $b_4$ are calibration coefficients determined by calibrating the responses J, $G_T N_t$ and W against the silicon content of known samples using regression analysis, J is the total number of gamma detector counts in unit time of gamma rays having an energy of 1.78 MeV, $G_T$ is the total number of counts in unit time of gamma rays having an energy in the window selected from said group, and $N_t$ is the observed thermal neutron flux in the sample during its irradiation with fast neutrons.

5. A method as defined in claim 1, in which the sample is a bulk sample and in which steps (a) and (b) are carried out at a first location, steps (c) and (d) are carried out at a second location which is remote from said first location, and said bulk sample is rapidly moved from said first location to said second location when steps (a) and (b) have been completed.

6. A method as defined in claim 4, in which said sample is being carried on a moving conveyor belt.

7. A method as defined in claim 6, in which steps (a) and (b) are carried out at a first location above or below said conveyor and steps (c) and (d) are carried out at a second location above or below said conveyor, said second location being downstream of said first location.

8. A method as defined in claim 4, in which said sample is the material in the wall of a borehole.

9. Apparatus for the simultaneous analysis of aluminium and silicon content of a sample of material using only a single irradiation from a single neutron source comprises:
   (a) a fast neutron source means for irradiating said sample of material;
   (b) a thermal neutron detector means located to monitor the thermal neutron flux in the irradiated sample which flux results from moderation of the fast neutrons within the sample material; and
   (c) a gamma ray detector means, separated from the neutron source and shielded therefrom, for monitoring the gamma spectrum from the irradiated sample, at least at 1.78 MeV and at an energy selected from the group consisting of (1) 1.015 MeV, (2) 0.844 MeV and (3) 1.015 MeV and 0.844 MeV.

10. Apparatus as defined in claim 9, including a sample container adapted to be movable quickly from a first location, in which it is positioned in close proximity to said fast neutron source means and said thermal neutron detector means, to a second location, remote from said first location, in which it is positioned in close proximity to said gamma ray detector means.

11. Apparatus as defined in claim 10, in which said container is mounted on a railway track.

12. Apparatus as defined in claim 10 or claim 11, wherein said sample container is a brass box.

13. Apparatus as defined in claim 9, in which said fast neutron source means and said thermal neutron detector means are mounted at a first location in close proximity to a conveyor belt adapted to transport said material, and said gamma ray detector means is mounted in close proximity to said conveyor belt in a second location which is downstream of said first location.

14. Apparatus as defined in claim 9, in which the fast neutron source, the thermal neutron detector and the gamma ray detector are mounted on a borehole probe.

15. Apparatus as defined in claim 14, in which said fast neutron source is encased in a cadmium shell.

16. Apparatus as defined in claim 15 including spectrum stabiliser means for stabilizing the spectrum from the irradiated sample.

17. Apparatus as defined in claim 16, including plural channel analyser means for monitoring the output of said gamma ray detector means and having channels responsive to the output of said gamma ray detector means when gamma radiation within a plurality of preselected energy windows is incident thereon, said energy windows including energy windows encompassing 0.844 MeV, 1.015 MeV and 1.78 MeV.

18. Apparatus as defined in claim 17, including (a) a plurality of counters, each counter being associated with a respective output of one of the channels of said plural channel analyser means, (b) a display device, and (c) a microprocessor programmed to derive, from the output of each said counter, values of the aluminium and silicon content of a material and to cause said display device to display and/or record said values.

19. Apparatus as defined in claims 17 or 18 wherein said multiple channel analyser means comprises a plurality of single channel analysers.

20. Apparatus as defined in claims 17 or 18 wherein said multiple channel analyser means comprises a multichannel analyser.

* * * * *